United States Patent
Binggeli et al.

(10) Patent No.: US 8,329,241 B2
(45) Date of Patent: Dec. 11, 2012

(54) BRASSICA SEEDS

(75) Inventors: Eva Binggeli, Maineville, OH (US);
Klaus Gassenmeier, Dübendorf (CH);
Jeff Molnar, Minneapolis, MN (US);
Peter Schieberle, Freising (DE)

(73) Assignee: Givaudan SA, Vernier (CH)

( * ) Notice: Subject to any disclaimer, the term of this patent is extended or adjusted under 35 U.S.C. 154(b) by 444 days.

(21) Appl. No.: 10/505,251

(22) PCT Filed: Feb. 26, 2003

(86) PCT No.: PCT/CH03/00142
§ 371 (c)(1),
(2), (4) Date: Oct. 29, 2004

(87) PCT Pub. No.: WO03/071863
PCT Pub. Date: Sep. 4, 2003

(65) Prior Publication Data
US 2005/0053714 A1    Mar. 10, 2005

(51) Int. Cl.
*A23L 1/22* (2006.01)
(52) U.S. Cl. ........ 426/629; 426/466; 426/469; 426/473; 426/481; 426/492; 426/494; 426/518; 426/520; 426/523; 426/650
(58) Field of Classification Search ............... 426/629, 426/650, 466, 469, 473, 481, 492, 494, 523, 426/518, 520
See application file for complete search history.

(56) References Cited

U.S. PATENT DOCUMENTS

| 3,574,640 A | | 4/1971 | Dougherty, Jr. ............ 99/140 |
| 3,697,290 A | * | 10/1972 | Lynn ............................ 426/550 |
| 6,013,304 A | * | 1/2000 | Todd ............................. 426/638 |
| 2005/0053714 A1 | | 3/2005 | Binggeli | |

FOREIGN PATENT DOCUMENTS

| WO | WO 96 38056 A | | 12/1996 |
| WO | 9805220 | * | 2/1998 |
| WO | 03041515 A1 | | 5/2003 |
| WO | WO 03 041515 A | | 5/2003 |

OTHER PUBLICATIONS

International Search Report for PCT/CH03/00142 dated Aug. 1, 2003.
XP-002249876, Odour-Active Compounds in Moderately Roasted Sesame, P. Schieberle, Institute fur Lebensmittelchemie, LichtenbergstraBe 4, D-85748 Garching, Germany, May 1995.
XP009014888, Investigations into Flavouring Compounds Formed in Roasted Brown Mustard, T.S. Vasundhara, Defence Food Research Laboratory, Mysore-10, India, Jul. 1981.

* cited by examiner

*Primary Examiner* — Helen F Heggestad
(74) *Attorney, Agent, or Firm* — Norris McLaughlin & Marcus PA

(57) ABSTRACT

Treated *Brassica* seeds and their extracts for use as a flavor and/or a flavor modifier in consumables. Treatment includes heating, and optionally grinding methods and/or recovery methods. Consumables include foods, beverages, health-care products, oral hygiene and oral care products, beauty-care products, and tobacco products. The extract contains elevated amounts of flavor and flavor modifier. One flavor modifier of the extract may be 2-furfurylthiol ("FFT"). A process for producing treated *Brassica* seeds extract.

19 Claims, No Drawings

BRASSICA SEEDS

This invention relates to treated *Brassica* seeds and their extracts, the process of forming such extracts and their use in consumables. The invention further relates to the production of 2-furfurylthiol ("FFT") by forming an extract of treated *Brassica* seeds.

The food industry is constantly searching for new flavors and flavor modifiers. In particular, consumers are increasingly demanding "all natural" consumable products. In many instances, in order for a consumable product to be labeled "all natural", the product may not include any synthetically made compounds. Accordingly, there is a growing demand for such flavor modifiers that are derived from natural sources.

Applicant has surprisingly found that when *Brassica* seeds are treated according to the methodology of the present invention described herein below, treated seeds or extracts thereof can be formed that display interesting flavor-modifying properties and these treated seeds or their extracts form a first aspect of the invention. The process of forming treated *Brassica* seeds or extracts thereof is a second aspect of the invention.

The applicant has additionally found that the amount of certain constituents of *Brassica* seeds which are present in small amounts in the seeds in their natural state may be elevated as a result of the treatment of the seeds according to the methodology of the present invention. One such interesting constituent is 2-furfurylthiol ("FFT"), which is an interesting flavor ingredient.

Whereas FFT is known to be present in plant products such as sesame seeds and coffee beans, and in meat products such as beef, pork, lamb and chicken, FFT can only be generated in tiny amounts by heating these sources.

Applicant has surprisingly found that not only is *Brassica* a source of FFT, but by treating the seeds in accordance with the inventive methodology, one can obtain relatively high amounts of this useful ingredient. Accordingly, in another aspect the invention provides a process of forming FFT.

The process of forming treated *Brassica* seeds according to the present invention comprises the step of heating *Brassica* seeds under a temperature and for a time sufficient to result in *Brassica* seeds having flavor modifying properties.

If desired, the treatment according to the invention may include heating the *Brassica* seeds in a surrounding temperature, with the surrounding temperature being within a range of about 120° C. to about 250° C. Typically, the *Brassica* seeds are heated in a fluid, with the fluid having a temperature in the range of from about 120° C. to about 250° C. A useful fluid is air.

With regard to time, if desired, the *Brassica* seeds may be heated for a period of time of at least about 5 minutes. Typically, the *Brassica* seeds are heated in the particular fluid for a period of time in the range of from about 5 minutes to about 60 minutes. If desired, the temperature and/or time may be adjusted so as to alter the flavor and/or aroma characteristics of the heated seeds. Typically, about 5 minutes to about 60 minutes are sufficient.

Any suitable, commercially available equipment, which allows for the control of temperature and time, may be used. Non-limiting examples include commercially available ovens and rotating drums. The particular heating unit may be a closed or airtight system, or an open system. In addition, any conventional heating method may be used to heat the seeds. Such methods include, but are not limited to, roasting, baking, frying, and microwaving. The *Brassica* seeds may be arranged within the heating vessel in any fashion.

Heat-treated *Brassica* seeds may be further treated by reducing the seeds to pieces or particles, thereby forming ground *Brassica* seeds. The treatment may include one or more of grinding, flaking, and expanding using commercially available equipment and methods well known in the art. In addition, if grinding is used, the *Brassica* seeds may be ground to an average particle size within a range of about 40 mesh to about 10 mesh. If desired, the seeds may be ground to an average particle size of about 20 mesh.

In many instances, it would be desirable to have an extract of the *Brassica* seeds. *Brassica* seeds treated according to the invention as described above, either whole or reduced to pieces or particles, may be further treated by subjecting them to a recovering treatment, thereby forming an extract. By the recovering treatment at least one of the constituents that was formed in the *Brassica* seeds as a result of the treatment according to the present invention is recovered.

If desired, the recovering treatment may include one or more of extracting, distilling, pressing, centrifuging, and chromatographically separating.

If extraction is used, the extracting step may include one or more of steeping, immersion, percolation, and batch extraction. If desired, an inert solvent may be used. By way of example, the inert solvent may include one or more of a vegetable oil, an alcohol, water, an aliphatic hydrocarbon, an oxygenated hydrocarbon, a triglyceride, and supercritical carbon dioxide. A useful solvent for extraction is vegetable oil. If desired, the inert solvent may have a temperature within a range of about 20° C. to about 70° C. In addition, during the extraction step, the treated *Brassica* seeds may be kept in the inert solvent for a period of time within a range of about 10 hours to about 36 hours.

The recovering step may include reducing the *Brassica* seeds to pieces or particles, for example by grinding or flaking, in an inert solvent. The grinding or flaking performed in this particular recovering step may be in place of, or in addition to, the step of reducing the *Brassica* seeds to pieces as described above.

In a particular method of forming an extract, *Brassica* seeds are heated for at least about 5 minutes in a surrounding temperature of about 160° C., and may then be ground or flaked. If the *Brassica* seeds are ground or flaked, the seeds may be ground or flaked either with or without the use of a solvent. Typically, a solvent is used because it dissipates the kinetic energy produced during the grinding or flaking process, thereby usually reducing the loss of various volable organoleptic compounds. If a solvent is used, the solvent may be inert. A useful solvent is vegetable oil.

If the seeds are ground, the seeds may be ground to an average particle size of from about 40 mesh to about 10 mesh. In one particular embodiment, the seeds are ground to an average particle size of about 20 mesh. If the seeds are flaked, the seeds may be flaked to an average thickness within a range of from about 0.010 inch to about 0.014 inch. In another particular embodiment, the particles have an average thickness of about 0.012 inch.

If an inert solvent is used in the grinding or flaking process, then the recovery process will begin during the grinding or flaking process. The recovery step may include one or more of extracting, distilling, pressing, centrifuging, and chromatographically separating, using any suitable commercially available equipment. If extraction is used, the extracting step may include one or more of steeping, immersion, percolation, and batch extraction. If steeping is used, ground, flaked, or expanded *Brassica* seeds may be steeped in an inert solvent, for example, a vegetable oil. The inert solvent may have a temperature of from about 20° C. to about 70° C.; and the seeds may be steeped for a period of time of from about 10 hours to about 36 hours. The solids may be separated from the solvent by filtration. If vegetable oil is used as the extracting solvent, no further processing is required after filtration.

However, if one or more other solvents are used such solvents may be removed by evaporation, so that the residue with extracted components of treated roasted *Brassica* seeds contains, for example, less than about 25 parts per million of the solvent. If ethanol is used, and if desired, the ethanol may be removed from the product using any suitable method, (e.g., evaporation), until the residue contains 15% (w/w) ethanol +/−2%.

If desired, sufficient vegetable oil is added to the residue to maintain a viscosity of less than about 100 centipoise in the extract.

In another aspect, the invention is directed to consumables and flavor preparations for consumables comprising treated *Brassica* seeds or extracts thereof. Treated *Brassica* seeds or extracts thereof may be added to or combined with consumables directly, or may be added to flavor preparations in an amount sufficient to impart, modify, enhance or mask flavor.

The amount may vary depending on the nature of the product and its application, as will be apparent to the skilled person.

For example, a useful amount of treated *Brassica* seeds or extracts thereof added to a preparation for a consumable may be at a concentration of about 0.1-25%, preferably about 0.5%-20%, more preferably about 5%-15% (w/w).

A useful amount of treated *Brassica* seeds or extracts thereof added to a consumable may be for example at a concentration of about 0.001% -5% (w/w), preferably about 0.005-2% (w/w), more preferably about 0.01-1% (w/w), most preferably about 0.125%-0.5 % (w/w). Typically, in the consumable, a concentration of about 0.01%-1% (w/w) to preferably about 0.125%-0.5 % (w/w) will be suitable for savory applications; a concentration of about 0.1-0.5 (w/w), preferably 0.2%-0.3% (w/w) will be suitable for soy products, a concentration of about 0.001 to 1% (w/w), preferably about 0.01%-0.2 % (w/w) will be suitable for dairy applications and beverage applications. For applications that need a high flavor impact including for example sauces, condiments, and cereals which are consumed together with other consumables, for example milk or noodles, and thereby thinned or diluted during consumption, suitable concentrations may be from about 0.1%-5% (w/w) or higher.

Consumables may include any product, which is capable of being placed in the oral cavity or ingested, regardless of whether it provides nutritive value and regardless of form. Examples include foods, beverages, health-care products, oral hygiene and oral care products, medicaments, beauty-care products, and tobacco products. Food products include for example prepared foods, sauces, soups, marinades, cereal products, rice products, popcorn products, breakfast cereals, cornflakes, tapioca products, sago products, baker's products, biscuit products, pastry products, bread products, confectionery products, desert products, gums, chewing gums, chocolates, ices, honey products, treacle products, yeast products, baking-powder, processed foods, cooked fruits and vegetable products, jellies, jams, fruit sauces, egg products, milk and dairy products, cheese products, butter and butter substitute products, milk substitute products, soy products, edible oils and fat products, sweeteners, nutraceutcals, gelatins, pharmaceutical and non-pharmaceutical gums, food extracts, plant extracts, meat extracts, and condiments.

Beverages include for example alcoholic drinks, beers, soft drinks, mineral and aerated waters and other non-alcoholic drinks, fruit drinks, fruit juices, coffee, artificial coffee, tea, cocoa, including forms requiring reconstitution, tablets, lozenges, drops, emulsions, elixirs, syrups and other preparations for making beverages.

Consumables particularly useful to combine with treated *Brassica* seeds or extracts thereof are savory products and food for preparation by microwave. Savory products include, for example, prepared foods, salt and spice products, vinegar products, sauces, soups, marinades, processed foods, meat and meat products, vegetable products, egg products, cooked vegetable products, soy products, edible oils and fat products, cheese products, yeast products; cereal products, butter and butter substitute products, food extracts, plant extracts, meat extracts, and condiments.

Treated *Brassica* seeds or extracts thereof may be particularly beneficial to add to products for preparation in the microwave, for example food products as mentioned herein above, which it may provide with roasted flavor and/or butter flavor notes usually missing in products prepared in the microwave.

Treated *Brassica* seeds or extracts thereof may be particularly beneficial to add to food and beverage products without butter or with a reduced amount of butter, which it may provide with butter flavor notes. Such products include for example bakery products, including biscuit products, pastry products, bread products, cakes, confectionery products, desert products, chocolates and ice cream, and beverage products such as milk shakes.

Another aspect of the invention is directed to a method of forming a consumable, comprising the step of combining a consumable and a flavor-imparting, -modifying, -enhancing, or -masking amount of treated *Brassica* seeds or extracts thereof.

Depending on the application, as will be apparent to a person skilled in the art, a combination of treated *Brassica* seeds with an extract of treated *Brassica* seeds may be used.

While not intending to be bound by theory, an important flavor and flavor modifier in *Brassica* seeds may be FFT. FFT is known as a flavor and applicant believes FFT may contribute to the flavor modifying properties applicant has found in *Brassica* seeds extract. Applicant believes that one or more precursors contained within the *Brassica* seeds chemically react upon heating the seeds, thereby forming flavors and flavor modifiers. For FFT, such a precursor may be a sulfur-containing precursor, and may be a sulfur-containing amino acid. One such precursor candidate is S-furfurylcysteine.

Not only does FFT provide desirable flavor and flavor-modifying characteristics, but also it is effective at extremely low concentrations. In particular, the odor threshold for FFT is 0.01 μg/L of water. Accordingly, FFT may be used in small amounts, thereby making its use highly cost-effective. In the past, the demand for FFT has been met by making FFT synthetically. However, in many situations and because of the increasing consumer-demand for "all natural" products, this no longer is an acceptable option. The process according to the present invention as described herein-above results in a significant percent-increase in the concentration of flavor and flavor modifiers including FFT. For example, the percent-increase may be at least 100%, at least 500%, at least 1000%, or at least 10,000%. If desired, the heated *Brassica* seeds may have a concentration of at least about 1 mg FFT per kg *Brassica* seeds. The heated *Brassica* seeds alternatively may have a concentration of at least about 5 mg FFT per kg seeds, or a concentration of at least about 10 mg FFT per kg seeds.

FFT may be extracted from *Brassica* seeds by the process according to the present invention as described herein above. The FFT contained in the treated *Brassica* seeds or their extract may be used in the form of treated *Brassica* seeds or their extracts according to the present invention as described herein above. In the alternative, FFT may be isolated by methods known in the art and used in isolated form.

A further aspect of the invention is directed to a flavor or a flavor modifier, or a consumable or preparation for a consumable containing such, comprising an elevated amount of FFT. FFT may be added in form of treated *Brassica* seeds or their extracts or in isolated form.

*Brassica* seeds added to consumables or preparations for consumables may have a concentration of at least about 1 mg FFT per kg seeds. Other useful concentrations of FFT may be a concentration of at least 5 mg FFT per kg seeds, or a concentration of at least 10 mg FFT per kg seeds.

The amount of FFT suitable in a product may vary depending on the nature of the product and its application, as will be apparent to the skilled person.

For example, a useful amount of FFT added to a preparation for a consumable may be at a concentration of about 5-20,000 (μg/kg), preferably about 50-5000 (μg/kg), more preferably about 250-3000 (μg/kg), most preferably about 500-1500 (μg/kg).

A useful amount of FFT added to a consumable may be for example at a concentration of about 0.1-2000 (μg/kg), preferably about 0.5-1000 (μg/kg), more preferably about 5-100 (μg/kg), most preferably about 10-50 (μg/kg).

As used herein, the term "*Brassica* seed" or "*Brassica* seeds" refers to one or more whole seeds of the *Brassica* genus within the family Brassicaceae (also known as the Cruciferae family). The *Brassica* seeds may be any seed type or combination of seed types within the *Brassica* genus. The *Brassica* genus includes the particularly useful mustard group within the *Brassica* genus, comprising *B. alba*, *B. hirta*, *B. juncea*, and *B. nigra*. Other examples for above-mentioned seeds include but are not limited to *Brassica adpressa*, *Brassica arvensis*, *Brassica campestris*, *Brassica cheiranthos*, *Brassica elongata*, subsp. *integrifolia*, *Brassica eruca*, *Brassica geniculata*, *Brassica kaber*, var. *pinnatifida*, *Brassica* var. *schkuhriana*, *Brassica napus*, *Brassica oleracea*, *Brassica orientalis*, *Brassica rapa*, and *Brassica toumefortii*. The genus- and species-names provided above comply with the International Code of Plant Nomenclature. Any of the seeds within the *Brassica* genus may be obtained through traditional commercial channels.

As used herein, the term "flavor modifier" means a material that enhances, masks or changes the flavor or fragrance of other materials. Enhancement means that a sensory sensation is perceived to be stronger or longer, or both. Masking relates to the complete or partial masking or weakening of off-tastes, which are tastes perceived as unpleasant. Masking is relevant for example in soy products, to mask the unpleasant off-taste of soybeans. Flavor modifiers according to the invention may include materials that have no perceivable own flavor or fragrance and merely enhance, mask or change the flavor or fragrance of other materials, and materials that additionally have their own flavor or fragrance notes.

"Flavor modifying properties" as used herein refers to one or more of the properties of a flavor modifier according to the present invention.

As used herein, the term "fluid" refers to any suitable gas, liquid, gas mixture, liquid mixture, vapor, aerosol, solution, dispersion, suspension, or the like, including air. The fluid temperature may be referred to as the "surrounding temperature".

The term "treated *Brassica* seeds" as used herein refers to *Brassica* seeds treated according to one or more steps of the present invention including heating the *Brassica* seeds as described herein above.

As used herein, the term "extract" means a preparation of one or more essential constituents of a botanical material typically separated by a solvent. The extract may be prepared from whole seeds, or the overall recovery process may include reducing the seeds to pieces or particles.

As used herein, the term "inert solvent" refers to any suitable solvent which does not chemically react with the desired extract components, especially flavors, flavor modifiers, or FFT. Non-limiting examples include vegetable oils, alcohols, water, aliphatic hydrocarbons, oxygenated hydrocarbons, triglycerides, supercritical carbon dioxide, and combinations thereof.

EXAMPLES

These examples are provided to help illustrate various aspects of the invention. However, the examples do not limit the scope of the invention. All of the seeds used in these working examples were obtained from Forbes Frozen Foods of Cincinnati, Ohio, USA, if not stated otherwise.

1. Heated *Brassica* Seeds, Concentration of FFT

Approximately 10 grams each of various types of *Brassica* seeds were heated as described in Table 1 below. Containers used had a loose-fitting cap to provide an open system. The concentration of FFT subsequently was determined by using a stable isotope dilution assay, although other procedures may be used, as known to those of ordinary skill.

The heated *Brassica* seeds were weighed and extracted with dichloromethane (50 ml) containing deuterated FFT ($[^2H_2]$-furfurylthiol, at a concentration of 20 μg per 50 mg). The volatile compounds subsequently were isolated by applying the high vacuum transfer technique described by Jung et al. (Lebensm.-Wiss. U Technol. 225:55-60, 1992), the Jung et al. article being incorporated in its entirety into this patent document by reference. The dichloromethane extract was placed into a high vacuum apparatus. The solvent and the volatiles were captured in a cooling trap which was cooled with liquid nitrogen to a temperature of −150° C. The resulting extract was dried over sodium sulfate and concentrated in a vigreux distillation column until enough solvent had been distilled off to a final volume of 1 ml. Subsequently, the extract was analyzed by gas chromatography/mass spectroscopy. The amount of FFT was calculated from the area m/z 81 for the analyte and m/z 83 for the internal standard.

TABLE 1

| Type of Seed | Type of Container | Temperature of Fluid in Container | Duration of Heat | Concentration FFT (mg per kg seeds) |
|---|---|---|---|---|
| *Brassica alba* (Example 1a) | 10 mL Pyrex | 200° C. | 10 minutes | 40 mg/kg |
| *Brassica napus* (Example 1b) | 10 mL Pyrex | 200° C. | 10 minutes | 9.2 mg/kg |
| *Brassica nigra* (Example 1c) | 10 mL Pyrex | 200° C. | 10 minutes | 8.2 mg/kg |

2. Concentration of FFT in Unheated *Brassica* Seeds

The concentration of FFT in unheated *Brassica* seeds was determined using a stable isotope dilution assay, as described in Example 1 above. In further detail, 300 g of *Brassica alba* seeds were extracted with dichloromethane containing 1 μg of labeled FFT. The remaining steps were performed as described in Example 1 above. Through this testing procedure, it was determined that the unroasted seeds contained less than 1 μg FFT per kg of seeds.

3. Roasted *Brassica Alba* Seeds 125 g of *Brassica alba* seeds were roasted in a Probat Sample Roaster (PRE 1Z, Probat-Werke von Gimbom Maschinenfabrik GmbH, Germany) at 160° C. for 10 minutes. The resulting seeds had a strong peanut-like aroma with chicken, sulfur, earthy, roasty, and popcorn by-notes, as determined by a panel of trained flavorists.

4. Roasted *Brassica Alba* Seeds 125 g of *Brassica alba* seeds were roasted in a Probat Sample Roaster (PRE 1 Z, Probat-Werke von Gimbom Maschinenfabrik GmbH, Germany) at 200° C. for 10 minutes. The resulting seeds had a strong coffee-like aroma, as determined by a panel of trained flavorists.

5. Roasted *Brassica Nigra* Seeds 125 g of *Brassica nigra* seeds were roasted in a Probat Sample Roaster (PRE 1 Z, Probat-Werke von Gimbom Maschinenfabrik GmbH, Germany) at 200° C. for 20 minutes. The resulting seeds had an aroma with very strong roasty and coffee notes, dominated with burnt sulfury, earthy, meaty, and caramel aspects, as determined by a panel of trained flavorists.

6. Roasted *Brassica Juncea* Seeds 125 g of *Brassica juncea* seeds were roasted in a Probat Sample Roaster (PRE 1Z, Probat-Werke von Gimbom Maschinenfabrik GmbH, Germany) at 160° C. for 10 minutes. The resulting seeds had an aroma with a very strong "oriental kitchen" note, as determined by a panel of trained flavorists.

7. Roasted *Brassica Rapa* Seeds 125 g of *Brassica rapa* seeds were roasted in a Probat Sample Roaster (PRE 1 Z, Probat-Werke von Gimbom Maschinenfabrik GmbH, Germany) at 160° C. for 10 minutes. The resulting seeds had an aroma with very strong roasty and meaty notes, as determined by a panel of trained flavorists.

8. Preparation of Encapsulated Roasted *Brassica Alba* Seeds Extract 125 g of *Brassica alba* seeds were roasted at 200° C. for 10 minutes in a Probat Sample Roaster (PRE1Z), and then ground in a coffee grinder (Moulinex Type 53402, Paris, France) to an average particle size of about 40 mesh. The ground seeds were subjected to an extraction process by adding 250 g of a vegetable oil (Miglyol 812 from Abitech Corporation of Columbus, Ohio) to the ground seeds. The seeds were steeped in a Certomat lab shaker (B. Brown Biotech International, Inc. Allentown, Pa.) at 50° C. for 20 hours. The extract was added to an aqueous solution of modified food starch, maltodextrin, and sugar, at total solids of 60%, and mixed with high shear in a Waring commercial blender (Blender 7012 Model 34BL21, Waring Products Division, Dynamics Corporation of America, New Hartford, Conn.) to form an emulsion (<3 Φm droplet size). This emulsion was then dried using an Anhydro PRD55 spray dryer (from APV Anhydro of Denmark) at an inlet air temperature of 340° F., an outlet air temperature of 210° F., and an atomizer wheel speed of 35,000 rpm. Powder containing 15% w/w flavor was recovered with a yield of 85%.

9. Encapsulated Roasted *Brassica Alba* Seeds Extract in an Instant Coffee

An instant coffee was prepared by mixing 1.58 g of Nestle Nescafe instant coffee powder (Nestle, Glendale, Calif.) with 0.02 g of the encapsulated *Brassica alba* seeds of Example 8. The powder mixture was dissolved in 180 ml of water, with the water having been heated to a temperature of 170° F. The resulting coffee had an aroma and taste which was both pleasing and stronger than that of the coffee without the encapsulated extract, as determined by a panel of trained flavorists.

10. Roasted *Brassica Nigra* Seeds in a Bouillon 500 g of *Brassica nigra* seeds were roasted in a circulating air oven (Memmet Type U50, Memmet, 854 Schwabach, Germany) at 200° C. or 60 minutes. The roasted seeds were ground in a coffee grinder (Moulinex Type 53402, Paris, France) to an average particle size of about 40 mesh. A bouillon base was prepared from the ingredients listed in Table 2 below. The fats were molten and combined. Then the turmeric powder was added and mixed until homogeneous. The remaining ingredients, which had been premixed, were added and mixed until homogenous. The mixture was left at a temperature of approximately 50-70° C. for 24 hours. Then the mixture was passed through a sieve to break any lumps. The bouillon was prepared by dissolving 22 g of bouillon base in 1000 ml of hot water. Then the ground seeds were added to the bouillon at a concentration of 50 g of ground seeds to 100 kg of the bouillon. The resulting bouillon exhibited a roasted chicken note with a roasted bone aspect, as determined by a panel of trained flavorists.

TABLE 2

| Ingredients of Bouillon Base | |
|---|---|
| | Weight (grams) |
| Salt (Sodium Chloride) | 350.0 |
| Corn Syrup Solids (Maltodextrin) | 408.0 |
| Lactose Monohydrate | 100.0 |
| Monosodium Glutamate | 70.0 |
| Beef Fat | 35.0 |
| Vegetable Fat | 20.0 |
| Burnt Sugar, Powder | 7.0 |
| Onion Powder | 5.5 |
| Nucleotides | 3.0 |
| Turmeric Powder | 1.5 |

11. Roasted *Brassica Nigra* Seeds in a Coffee-Flavored Yogurt 500 g of *Brassica nigra* seeds were roasted in a circulating air oven (Memmet Type O50, Memmet, 854 Schwabach, Germany) at 200° C. for about 20 minutes. The roasted seeds then were ground in a coffee grinder (Moulinex Type 53402, Paris, France) to an average particle size of about 40 mesh. The ground seeds were added to a coffee flavor at 10% (w/w). The coffee flavor was coffee paste flavor, commercially available under the product code 96504789 from Givaudan, Ueberlandstrasse CH-8600 Duebendorf, Switzerland. The resulting coffee flavor was added to yogurt at a concentration of 0.5% (w/w), and compared with the same yogurt containing the same coffee flavor without the roasted *Brassica nigra* seeds. The yogurt, itself, was a set-type yogurt, commercially available from Swiss Dairy Foods of Ostermundigen, Switzerland, under the product name Tony Jogurt Natur. The yogurt which contained the coffee flavor which had been modified with the ground seeds exhibited stronger coffee notes and a longer lasting coffee aftertaste relative to the yogurt, which had been flavored with the plain coffee flavor, as determined by a panel of trained flavorists.

12. Roasted *Brassica Nigra* Seeds in a Cream Soup Base 500 g of *Brassica nigra* seeds were roasted in a circulating air oven (Memmet Type O50, Memmet, 854 Schwabach) at 200° C. for 60 minutes. The roasted seeds were ground in a coffee grinder (Moulinex Type 53402, Paris, France) to an average particle size of about 40 mesh. A cream soup base was prepared from the ingredients listed in Table 3. All dry ingredients (except roux) were mixed, and molten fat was well dispersed in the blend. The mixture was sieved, the roux was added, and this subsequent blend was mixed well. The cream soup was prepared by dissolving 50 g cream soup base in 500 ml of hot water. Then the ground seeds were added to the cream soup at a concentration of 50 g of ground seeds to 100 kg of cream soup. The resulting cream soup exhibited a roasted chicken note with a roasted bone aspect, as determined by a panel of trained flavorists.

TABLE 3

Ingredients of Cream Soup Base

|  | Amount (grams) |
| --- | --- |
| Roux* | 483.35 |
| Starch, Native | 150.00 |
| Corn Syrup Solids (Maltodextrin) | 88.32 |
| Salt (Sodium Chloride) 0.4 mm | 78.65 |
| Whipping Agent | 66.65 |
| Skim Milk Powder | 66.65 |
| Monosodium Glutamate | 33.35 |
| Yeast Extract | 8.35 |
| Sugar, Extra Fine | 8.35 |
| Vegetable Fat | 8.30 |
| Xanthan Gum | 6.65 |
| Citric Acid, Anhydrous | 0.80 |
| Pepper Granuseal (may be purchased from Givaudan Flavor Corp, USA) | 0.26 |
| Bay leaf Granuseal (may be purchased from Givaudan Flavor Corp, USA) | 0.13 |
| Turmeric (may be purchased from Givaudan Flavor Corp, USA) | 0.12 |
| Nutmeg Granuseal (may be purchased from Givaudan Flavor Corp, USA) | 0.07 |

*Roux was prepared from wheat flour (640 g) and vegetable fat (360 g; mp. 42° C.). The fat was molten at 60° C. and mixed with flour to yield a homogeneous paste. The paste was allowed to cool overnight and subsequently was shredded into small granules having a diameter of about 2–3 mm.

13. The Eight Main Flavorants Formed by Roasting *Brassica Alba* at 200° C. for 10 Minutes Approximately 5 g of *Brassica alba* seeds were put into a test tube (16 cm×1.5 cm inner diameter) to a height of about 3 cm. The test tube was closed with aluminum foil and heated in an aluminum thermoblock (Fa. Liebisch, Type 2090, Bielefeld, Germany) at 200° C. for 10 minutes. Following this treatment, an extract was prepared using 100 g of roasted *Brassica alba* seeds. These seeds were frozen using liquid nitrogen and then were ground. The ground seeds were extracted three times for 30 minutes with 100 ml of diethyl-ether. The combined diethylether phases were concentrated on a Vigreux distillation column to a residual volume of 150 ml. The volatile compounds were isolated by distillation in vacuo, as described by Jung et al., see Example 1 for the citation to the Jung et al. article. Then an aroma extract dilution analysis ("AEDA") was performed to determine the flavor-dilution ("FD") factor for each of several compounds, according to the AEDA methodology described in the textbook by Peter Schieberle entitled *Characterization of Food: Emerging Methods*, Gaonkar AG (editor), pp. 403-431, 1995. Pages 403-431 of the Schieberle article are expressly incorporated into this patent document by reference. Those flavorants which had a FD factor greater than 128 are shown in Table 4 below. The data shown in the Table indicate that, based on FD-factor, FFT is the most important odorant/flavorant compound extracted from the roasted *Brassica alba* seeds, as determined by AEDA. The odor qualities of the compounds listed in Table 4 were determined by a panel of trained flavorists.

TABLE 4

| Compound | Odor Quality | FD-Factor |
| --- | --- | --- |
| 2-Furfurylthiol (FFT) | roasty, coffee-like | 4096 |
| Methional | potato-like | 1024 |
| 4-Hydroxy-2,5-dimethyl-3(2H)-furanone | caramel-like | 512 |
| 3-Methylbutanal | malty | 256 |
| 2,3-Pentandione | buttery | 256 |
| 3-Mercapto-2-pentanone | sulfury | 256 |
| 2-Acetyl-2-thiazoline | popcorn-like | 256 |
| 3-Hydroxy-4,5-dimethyl-2(5H)-furanone | seasoning-like | 256 |

14. Concentration of FFT in Roasted *Brassica* Seeds Under Different Temperature and Time Conditions This example was performed using *Brassica alba* seeds. For each time and temperature condition shown in Table 5 below, *Brassica alba* seeds were placed in a test tube (16 cm×1.5 cm inner diameter) to a height of 3 cm, and the test tube was closed with aluminum foil. Each test tube contained approximately 5 mg of seeds. A thermoblock (Fa. Liebisch, Type 2090, Bielefeld, Germany) was used for heating. The concentration of FFT in the roasted seeds were determined using a stable isotope dilution assay, as described in Example 1 above.

TABLE 5

| Temperature (° C.) | Duration (Min.) | FFT Concentration (µg/kg) |
| --- | --- | --- |
| 160 | 5 | <1 |
| 160 | 10 | 108 |
| 160 | 20 | 1706 |
| 200 | 5 | 514 |
| 200 | 10 | 3892 |
| 200 | 20 | 11453 |
| 240 | 5 | 3550 |
| 240 | 10 | 19507 |
| 240 | 20 | 3663 |

15. Forming of an Extract of Roasted *B. juncea* Seeds

*B. juncea* seeds (may be purchased from Forbes Foods, Terrace Park, Ohio, USA under the name "Oriental Mustard seeds") were roasted at 390° F. for 20 minutes, then cooled to 200° F. An extract from these roasted *B. juncea* seeds was formed by adding double the weight of miglyol oil and reducing the seeds to smaller particles in a chopper while steeping in the Miglyol oil for 60 minutes at 225° F. From the resulting slurry, solid particles were removed by centrifugation. The roasted *B. juncea* seeds extract was collected.

16. Extract of Roasted *B. juncea* in Chicken Gravy Base.

An extract of roasted *B. juncea* seeds was prepared as described in example 15.

The extract was added to a brown chicken gravy base at a concentration of 0.15%. The chicken gravy base was prepared as indicated in table 6.

TABLE 6

| Premix Ingredient | Grams |
| --- | --- |
| Water | 88.16 |
| Modified Cornstarch (National 465, National Starch & Chemical, USA) | 3.25 |
| Soybean Oil | 3.00 |
| Nat. Chicken Broth Flavor (may be purchased from Givaudan Flavor Corp, USA) | 1.75 |
| Autolyzed Yeast Extract (may be purchased from Givaudan USA) | 0.75 |
| Nat. Vegetable Flavor (may be purchased from Givaudan Flavor Corp, USA) | 0.70 |

TABLE 6-continued

| Premix Ingredient | Grams |
| --- | --- |
| Salt | 0.60 |
| All Purpose Flour | 0.50 |
| Garlic Powder (may be purchased from Gilroy foods, USA) | 0.40 |
| Onion Powder (may be purchased from Gilroy foods, USA) | 0.40 |
| Emulsifier, Soy Lecithin (may be purchased from Central Soya, USA under the name "Centrolex") | 0.25 |
| Celery Salt (may be purchased from McCormick, USA) | 0.15 |
| Black Pepper (may be purchased from McCormick, USA) | 0.05 |
| Caramel Color, (may be purchased from Sethness Caramel Color, USA under the name "Sethness RT325") | 0.04 |
|  | 100.00 |

The prepared brown chicken gravy base was compared with the same brown chicken gravy base without the extract. In comparison, the brown chicken base with the extract exhibited a flavor modifying effect with a higher overall flavor impact and was described as mouthwatering, as determined by a panel of trained flavorists.

17. Extract of Roasted *B. juncea* in Veggie Patties

An extract of roasted *B. juncea* seeds was prepared as described in example 15.

The extract was added to veggie patties at a concentration of 0.25%. The veggie patties were prepared according to table 7. A first portion of water and soy protein was combined and the soy protein was hydrated by mixing for 10 minutes. The remaining dry ingredients were added. A second portion of water was combined with methylcellulose using a hand mixer, thereby forming hydrated methylcellulose. The hydrated methylcellulose was added to the hydrated soy protein and mixed using a hand mixer at low speed for 10 minutes, forming a mixture. The vegetable oil was added to the mixture and mixed well. The mixture with oil was formed into 100 g patties with 3.5 inch diameter. The patties were baked at 425° F. for 10 minutes to an internal temperature of 170° F. The baked patties were frozen. Frozen patties were reheated by baking at 425° F. for 15 minutes.

TABLE 7

| Water, first portion | 34.40 |
| --- | --- |
| Soy Protein Concentrate, Response 4402 (may be purchased from Central Soya, USA) | 15.00 |
| Soy Protein Concentrate, Response 4320 (may be purchased from Central Soya, USA) | 8.99 |
| Nat. Beef Type Flavor | 3.42 |
| Black Pepper, ground | 0.04 |
| Salt | 0.50 |
| Vegetable Oil | 2.25 |
| Water, second portion | 34.40 |
| Methylcellulose, Methocel E461(may be purchased from Dow Chemical company, USA) | 1.00 |
|  | 100.0 |

The veggie patties with 0.25% extract were compared with the same veggie patties without the extract. In comparison, the veggie patties with the extract exhibited a flavor modifying effect perceived as a higher overall flavor impact and a mouthwatering effect, as determined by a panel of trained flavorists.

18. Sensory Evaluation of *Brassica juncea* Extract Compared to Flavor Modifier Ribotide in Veggie Patties A Short-cut signal detection measure with R-index Analysis was performed with the following samples: roasted *B. juncea* seeds extract and Ribotide® (50:50 co-crystalline mixture of disodium 5'-guanylate and disodium 5'-inositate). Ribotide® was obtained from Nomura (formerly Takeda), USA), in Veggie Patties. Veggie Patties were prepared as described in example 15. Roasted *B. juncea* seeds extract was prepared as described in example 15.

Forty panelists experienced in discrimination tests evaluated the samples with the six replications in separate tasting booths under white light. The panelists were drawn from a population of 90 employees screened for sensory acuity and experienced in difference testing. Distilled water for rinsing between samples, plain oyster crackers for cleansing the palate, and expectoration cups were provided. All samples were portioned in flavorless, odorless 2 oz plastic cups and served at approximately 140° F. The panelists were instructed to evaluate a test sample compared to a reference sample labeled "reference" for similarity or difference in overall flavor. The test samples, including blind controls (Veggie Patties without additions), were presented to the panelists in balanced-randomized order for paired comparison to the reference sample. The panelists were asked to indicate whether the test sample was the same as or different from the reference, and to rate how sure they were of their decision. For this sureness rating, there were three degrees of sureness each, i.e. "same—sure", "same—unsure", "same—very unsure", "different—sure", "different—unsure", and "different—very unsure".

The protocol used the R-index rating procedure for short-cut detection measures as reported by M. O'Mahony (1979), "Short-cut signal detection measures for sensory analysis", Journal of Food Science 44 (1), 302-303; and J. Bi, and M. O'Mahony (1995), "Table for testing the significance of the R-index", Journal of Sensory Studies 10, 341-347.

R-index is the probability of correctly choosing one of two samples in a paired comparison presentation, i.e. between the reference and each sample. If R=100%, then the samples are perfectly different, if R=50%, then samples are distinguishable only by chance. The greater R, the greater the differences between the sample and the reference.

Statistical tests were performed using SPSS software (version 9.0, SPSS Inc., Chicago Ill.) to perform an ANOVA analysis with a significance level set at $P<0.001$ and 0.05, respectively.

The R-index values for all samples and blind controls along with the significance of the differences among the test samples and blind control are shown in Table 6.

The R-index for roasted *B. juncea* extract was 73% and significantly different from the blind control at 50% and Ribotide 0.2% at 63%. The Ribotide 0.25% with an R-index of 66% was not significantly different from the Ribotide 0.2 % sample at 63%, and not significantly different from *Brassica* extract sample at 73%.

The difference from the blind control for roasted *B. juncea* extract was significantly higher than for Ribotide 0.2% but not significantly higher than from Ribotide 0.25%. Therefore, roasted *B. juncea* extract performed comparable to Ribotide 0.25% in this test.

TABLE 6

R-Index values calculated from the distribution of ratings by replications for the samples.

| Samples | R-Index Values[1] [%] |
| --- | --- |
| Blind control (without additions) | 50%c |
| Roasted *B. juncea* extract 0.25% | 73%a |
| Ribotide 0.25% | 66%ab |
| Ribotide 0.20% | 63%b |

[1]R-Index values with the same letters are not significantly different at the $P < 0.05$ level.

What is claimed is:

1. A process of treating *Brassica* seeds, comprising the step of:
   heating whole *Brassica* seeds, under a temperature and for at least 10 minutes to result in *Brassica* seeds having flavor modifying properties wherein the whole *Brassica* seeds are heated to a temperature within a range of from about 160° C. to about 250° C.

2. A process according to claim 1 wherein Brassica seeds are heated at a surrounding temperature within a range of about 160° C. to about 250° C. and for a period of time of at least about 10 minutes.

3. A process according to claim 1, comprising the step of;
   further treating the *Brassica* seeds by reducing the seeds to pieces or particles.

4. A process according to claim 1 further comprising the step of:
   forming an extract of the treated *Brassica* seeds.

5. A process according to claim 4 wherein the method of forming the extract is selected from extracting, distilling, pressing, centrifuging, and chromatographically separating, extracting including one or more of steeping, immersion, percolation, and batch extraction; extracting including steeping the treated *Brassica* seeds in an inert solvent, extracting including steeping in one or more of a vegetable oil, an alcohol, water, an aliphatic hydrocarbon, an oxygenated hydrocarbon, a triglyceride, and supercritical carbon dioxide; extracting including steeping in a vegetable oil.

6. Treated *Brassica* seeds produced by the process according to claim 1.

7. An extract of treated *Brassica* seeds extracted from the treated *Brassica* seeds according to claim 6.

8. Treated *Brassica* seeds according to claim 6 comprising 2-furfurylthiol, wherein the 2-furfurylthiol concentration in the product corresponds to at a concentration of at least 1 mg 2-furfurylthiol per kg *Brassica* seeds.

9. Treated *Brassica* seeds according to claim 6 comprising 2-furfurylthiol, wherein the concentration of 2-furfurylthiol in the product is at least 1 mg per kg product (w/w).

10. A preparation for consumables comprising treated Brassica seeds according to claim 6 at a concentration of 5-20,000 µg/kg of the preparation.

11. Treated *Brassica* seeds according to claim 6 wherein the *Brassica* seeds are selected from the group consisting of *Brassica alba, Brassica juncea, Brassica napus, Brassica nigra, Brassica rapa*, and combinations thereof.

12. A consumable or a flavor preparation for consumables, comprising treated *Brassica* seeds produced by the process of claim 1 or an extract thereof.

13. A consumable according to claim 12 comprising treated *Brassica* seeds or extracts thereof at a concentration of 0.001%-5% (w/w).

14. A flavor preparation for consumables according to claim 12 comprising treated *Brassica* seeds or extracts thereof at a concentration of 0.1-25% (w/w).

15. A method of forming a consumable comprising the step of:
   combining a consumable and a flavor-imparting, -modifying, -enhancing or -masking amount of treated *Brassica* seeds produced by the process of claim 1, or extracts thereof.

16. A process for forming 2-furfurylthiol according to the process of claim 1.

17. A process according to claim 16 wherein the heat-treatment results in a percent increase in the concentration of 2-furfurylthiol of at least 100 percent.

18. 2-furfurylthiol formed by the process according to claim 16.

19. A process according to claim 1 wherein the *Brassica* seeds are selected from the group consisting of *Brassica alba, Brassica juncea, Brassica napus, Brassica nigra, Brassica rapa*, and combinations thereof.

* * * * *